US00PP13748P39

(12) United States Plant Patent
Scheffers

(10) Patent No.: US PP13,748 P3
(45) Date of Patent: Apr. 29, 2003

(54) DRACAENA PLANT NAMED '0102RB'

(76) Inventor: Ruud A. M. Scheffers, Plaats 9, 2675 CK, Honselersdijk (NL)

( * ) Notice: Subject to any disclaimer, the term of this patent is extended or adjusted under 35 U.S.C. 154(b) by 0 days.

(21) Appl. No.: 09/962,431

(22) Filed: Sep. 26, 2001

(65) Prior Publication Data

US 2002/0166154 P1 Nov. 7, 2002

(30) Foreign Application Priority Data

Feb. 26, 2001 (EP) ..... 2001/0356

(51) Int. Cl.[7] ..... A01H 5/00
(52) U.S. Cl. ..... Plt./383

(58) Field of Search ..... Plt./383

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named '0102RB' characterized by its leaf coloration which is unlike any other known *Dracaena Vand. Ex. L. fragrans* (group Compacta) variety; leaf margin is approximately 1 mm to 10 mm in width and dark green (RHS 139 A), center stripe is approximately 2 to 10 mm in width and greyish green very fine stripes (between RHS 189 A and 190 D); two other stripes between center stripe and margin are approximately 1 to 5 mm in width and pure white; and the stripe between the pure white stripe and the center stripe is green (RHS 145 A), approximately 5 to 10 mm in width with very fine white lines.

2 Drawing Sheets

LATIN NAME OF THE GENUS AND SPECIES OF THE PLANT CLAIMED

*Dracaena Vand. Ex. L. fragrans* (group Compacta)

VARIETY DENOMINATION

0102RB

BACKGROUND OF THE INVENTION

The present invention comprises a new and distinct cultivar of Dracaena plant botanically known as *Dracaena Vand. Ex. L. fragrans* (group Compacta) and hereinafter referred to by the cultivar name '0102RB'.

The new cultivar was selected by the inventor, Ruud A. M. Scheffers, in Honselersdijk, in 2000. The new cultivar was obtained as a natural mutation of *Dracaena Vand. Ex. L. fragrans* (group Compacta with cultivar name 'Compacta Variegata'.

The new cultivar was first asexually propagated by the inventor in Honselersdijk, The Netherlands, in 1998. Subsequent asexual reproduction of the new cultivar by division has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish '0102RB' as a new and distinct cultivar:

1. leaf coloration which is unlike any other known *Dracaena Vand. Ex. L. fragrans* (group Compacta) variety;
2. leaf margin is approximately 1 mm to 10 mm in width, and dark green (RHS 139 A);
3. Center stripe is approximately 2 to 10 mm in width, and greyish green very fine stripes (between RHS 189 A and 190 D);

4. two other stripes between center stripe and margin are approximately 1 to 5 mm in width of pure white; and
5. the stripe between the pure white stripe and the center stripe is green (RHS 145 A), approximately 5 to 10 mm in width with very fine white lines.

'0102RB' has not been observed under all possible environmental conditions. The phenotype on the new cultivar may vary significantly with variations in environment such as temperature, light intensity, and daylength without any change in genotype. The following observations, measurements and values describe plants grown in Honselersdijk, The Netherlands under greenhouse conditions which closely approximate those generally used in horticultural practice.

In comparison with the well-known Dracaena cultivar *Dracaena Vand. Ex. L. fragrans* (group Compacta) 'Compacta Variegata' (unpatented), '0102RB' has similar shaped and structured leaves but the coloration is entirely different.

| | '0102RB' | 'Variegata Compacta' |
|---|---|---|
| leaf color upper side | | |
| margin | Approximately 1 mm to 10 mm in width of dark green (RHS 139 A) | approximately 11 mm in width of dark green (RHS 137 A) |
| stripes next to margin | Approximately 1 to 5 mm in width of pure white (no RHS comparable color) | approximately 1 to 4 mm in width of pure white (no comparable RHS color) |
| stripes between white and center | Approximately 5 to 10 mm in width of basically green (RHS 145 A) with very fine white lines | — |
| center stripe | Approximately 2 to 10 mm in width of greyish green very fine stripes (between RHS 189 A and 190 D) | approximately 20 mm in width consisting of grey green lines (RHS 189 B and C and 139 A) |
| leaf color | | |

-continued

| | '0102RB' | 'Variegata Compacta' |
|---|---|---|
| under side | | |
| margin | similar though less glossy and slightly lighter of color | similar in width as upper side but green (RHS 137 A) |
| stripe next to margin and stripe between white and center stripe | similar as upper side | similar of upper side |
| center stripe | contrary to upper side the midrib is visible and approximately 4 mm in width and green (RHS 137 C) | contrary to upper side the midrib is visible and approximately 4 mm in width in green (RHS 138 B) surrounded by approximately 4 mm wide greyish green stripes (RHS 189 B and 139 C and green with greyish glare (no comparable RHS color) |

BRIEF DESCRIPTION OF THE DRAWING

The accompanying photographs illustrate a 16-weeks old plant of Dracaena '0102RB', with colors being as true as possible with illustrations of this type. The first drawing shows a 16-weeks old plant of Dracaena '0102RB'. The second drawing shows a 16-weeks old plant of '0102RB' propagated from a top together with a 16-week old plant of 'Compacta Variegata' propagated from a tip.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Parentage: *Dracaena Vand. Ex. L. fragrans* (group Compacta) 'Compacta Variegata'.

Propagation: Primarily by vegetative division of the plant head or apical meristem.

General observations:

*Growing conditions.*—'0102RB' is grown in a greenhouse. The grower propagates '0102RB' in a normal commercial greenhouse under temperatures of 20–21 degrees Celsius day and night. As with most Dracaena varieties, '0102RB' does not stand direct sunlight so sun shields are closed when sunlight becomes to bright. No artificial lighting or photoperiodic treatments are conducted. Highest temperature resistance is at least 40 degrees Celsius, lowest is 5 degrees Celsius. Resistance, tolerance and susceptibility to stresses, pathogens and pests is very good. Compound fertilizer is added to the soil. There are no other cultural or environmental treatments.

*Plant vigor.*—Good.

Plant habit:

*Growth rate.*—Mature plant growth approximately 20 weeks from the planting of a rooted cutting.

*Form.—Compact.*

*Plant height.*—Approximately 17 to 19 cm in a 17 cm pot (16-weeks old and grown from a top).

*Plant width.*—Approximately 35 to 40 cm in a 17 cm pot (16-weeks old and grown from a top).

Leaves:

*Form and size.*—Ensiform with accuminate tip, cuneate base. Length is approximately 22–25 cm, width is approximately 4 cm to 4.5 cm.

*Leaf arrangement.*—Spiral.

*Texture.*—Strong and leathery, lightly ribbed.

*Veins.*—One main vein, visible only on the underside of the leaf (mid-rib), RHS 137 C.

*Margin.*—Entire, lightly curled and thinner than center of leaf.

*Thickness.*—Medium.

*Number.*—Approximately 25 leaves per plant when grown in a 17 cm pot for 16 weeks in The Netherlands.

Flowers: No flowers observed, this species only flowers when growing conditions are very poor.

Stem:

*Length.*—Approximately 3 cm.

*Diameter.*—1.5 cm and formed by bases of leaves.

*Color.*—Pure white to green (RHS 145 A).

*Other.*—Strong.

Roots: Orange-brown (RHS 168 D) in color, it takes approximately 3 weeks to initiate roots and approximately 7 weeks are needed to produce a rooted liner.

Plant disease/insect tolerance: '0102RB' has a very high resistance against diseases and a very high tolerance against insects.

Reproductive organs: No flowers observed, this species only flowers when growing conditions are very poor.

I claim:

1. A new and distinct cultivar of Dracaena plant named '0102RB', as described and illustrated herein.

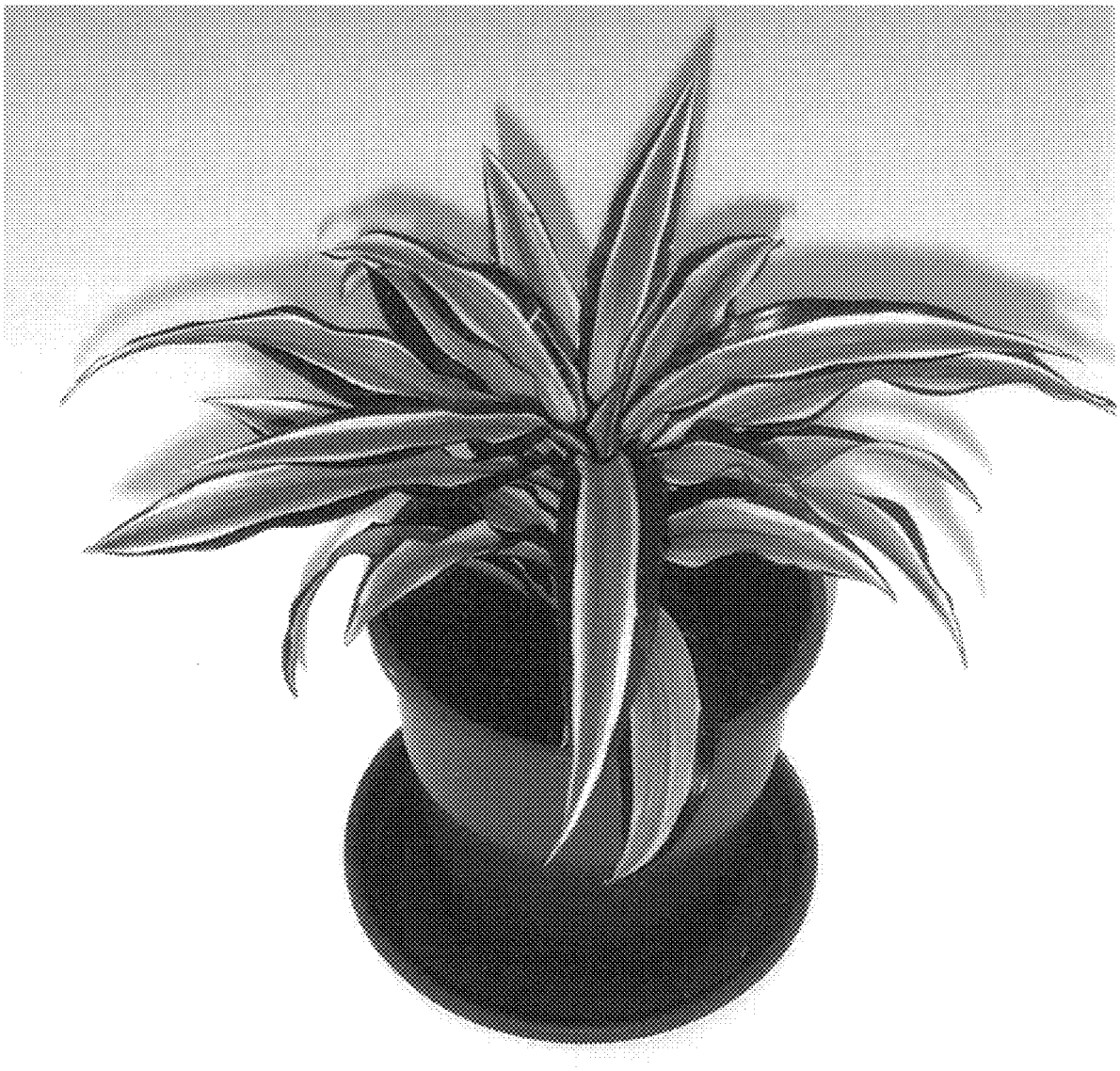

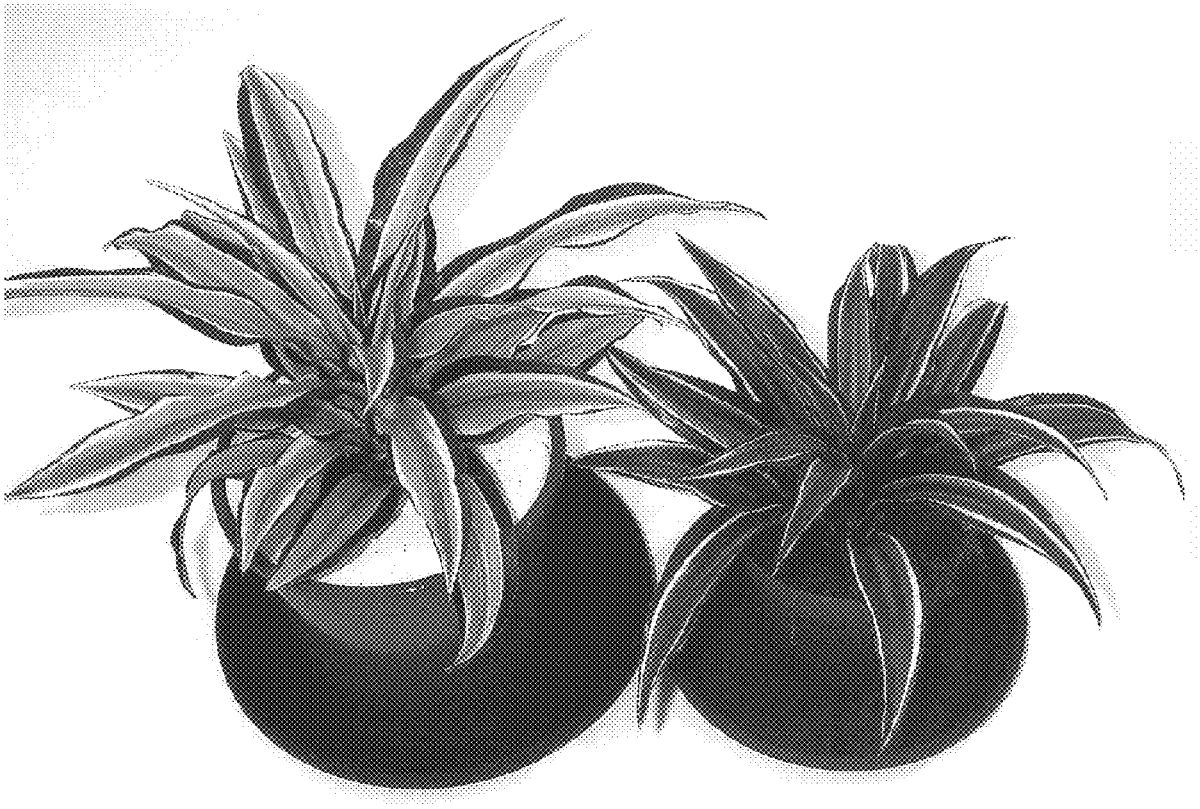

* * * * *